United States Patent
Clark et al.

(10) Patent No.: US 6,677,490 B2
(45) Date of Patent: Jan. 13, 2004

(54) METHOD FOR PRODUCING ALCOHOL/KETONE MIXTURES

(75) Inventors: James Clark, Yorkshire (GB); Eric Fache, Caluire et Cuire (FR); Ducan Macquarrie, Yorkshire (GB); Peter Price, Yorkshire (GB); John Rafelt, Dorset (GB)

(73) Assignee: Rhodia Polyamide Intermediates, Saint Fons (FR)

( * ) Notice: Subject to any disclaimer, the term of this patent is extended or adjusted under 35 U.S.C. 154(b) by 0 days.

(21) Appl. No.: 10/149,650

(22) PCT Filed: Dec. 14, 2000

(86) PCT No.: PCT/FR00/03517
§ 371 (c)(1),
(2), (4) Date: Oct. 15, 2002

(87) PCT Pub. No.: WO01/44153
PCT Pub. Date: Jun. 21, 2001

(65) Prior Publication Data
US 2003/0097025 A1 May 22, 2003

(30) Foreign Application Priority Data
Dec. 17, 1999 (FR) ............................................. 99 16010

(51) Int. Cl.[7] ..................... C07C 45/41; C07C 29/20; C07C 35/08; C07F 9/00; C07F 1/08
(52) U.S. Cl. ..................... 568/344; 568/346; 568/354; 568/835; 568/836; 556/42; 556/56; 556/57; 556/113; 556/137; 556/150
(58) Field of Search ............................ 568/344, 346, 568/354, 835, 836; 556/42, 56, 57, 113, 137, 150

(56) References Cited

U.S. PATENT DOCUMENTS

| | | | |
|---|---|---|---|
| 3,925,316 A | * | 12/1975 | Brunie et al. ............... 260/586 |
| 3,987,100 A | * | 10/1976 | Barnette et al. |
| 4,238,415 A | * | 12/1980 | Bryan |
| 4,720,592 A | * | 1/1988 | Besmar et al. ............... 568/342 |
| 5,298,665 A | * | 3/1994 | Janssen et al. ............... 568/342 |
| 5,859,301 A | * | 1/1999 | Kragten et al. ............... 568/342 |
| 6,160,183 A | * | 12/2000 | Druliner et al. |

FOREIGN PATENT DOCUMENTS

| | | |
|---|---|---|
| EP | 0 367 326 | 5/1990 |
| EP | 0 428 803 | 5/1991 |
| EP | 0 453 021 | 10/1991 |
| WO | WO 92/16487 | 10/1992 |

OTHER PUBLICATIONS

I.C. Chisem et al., "Catalytic oxidation of alkyl aromatics using a novel silica supported Schiff base complex," *Chem. Commun.* (Cambridge) (1998), vol. 18, pp. 1949–1950, XP002149029.

\* cited by examiner

*Primary Examiner*—James O. Wilson
*Assistant Examiner*—Sikarl A. Witherspoon
(74) *Attorney, Agent, or Firm*—Burns, Doane, Swecker & Mathis, L.L.P.

(57) ABSTRACT

The invention relates to a method for producing a mixture of alcohols/ketones by decomposing an alkyl hydroperoxide, particularly to a method for producing a cyclohexanol/cyclohexanone by decomposing cyclohexyl hydroperoxide in the presence of a heterogeneous catalyst. According to the invention, the reaction is carried out in the presence of a heterogeneous catalyst containing an organometallic segment fixed on the surface of a porous solid compound such as silicon. The organometallic segment can be formula (I).

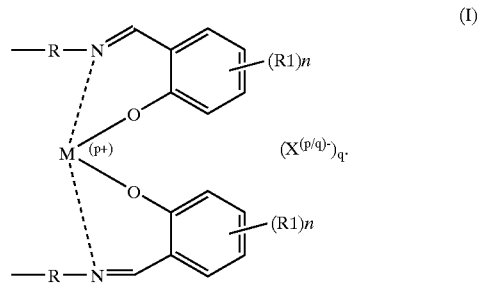

9 Claims, No Drawings

METHOD FOR PRODUCING ALCOHOL/KETONE MIXTURES

The invention relates to a process for the preparation of an alcohol/ketone mixture by decomposition of an alkyl hydroperoxide.

It relates more particularly to the preparation of a cyclohexanol/cyclohexanone mixture by decomposition of cyclohexyl hydroperoxide in the presence of a heterogeneous catalysis.

Among these organic hydroperoxides, cyclohexyl hydroperoxide is prepared by the oxidation of cyclohexane. It results, by catalytic decomposition, in cyclohexanone and cyclohexanol.

Industrial processes for the production of these cyclohexanol/cyclohexanone mixtures are of very great economic importance as they make possible access to the manufacture of chemicals on a large scale, such as adipic acid. These processes are described in an extensive literature, both scientific articles and patents.

The conventional industrial process consists of an oxidation of cyclohexane by air, making it possible to obtain a mixture of compounds, including cyclohexyl hydroperoxide (CHHPO), alcohols, ketones and acids. Cyclohexyl hydroperoxide is converted to a cyclohexanol/cyclohexanone mixture by various reactions, such as hydrogenation or decomposition.

The decomposition of organic hydroperoxides and in particular of cyclohexyl hydroperoxide (CHHPO) can first of all be carried out by homogeneous catalysis, that is to say in the presence of a catalyst dissolved in the reaction medium. Thus, Patent FR-A-1 580 206 discloses the oxidation of a cycloalkane in the liquid phase, followed by heating the solution thus obtained of the cycloalkyl hydroperoxide in the cycloalkane in the presence of a soluble chromium derivative as catalyst. Likewise, the articles in the Journal of the American Chemical Society (1985), 107, pages 3534 to 3540, or in the Journal of Molecular Catalysis (1988), 48, pages 129 to 148, describe the use of organic salts, such as cobalt octanoate, or of complexes dissolved in the organic liquid phase where the reaction takes place or in an aqueous phase in contact with the said organic phase.

This decomposition of cyclohexyl hydroperoxide can also be carried out by neutralization of the acids present in the medium with an alkaline hydroxide and in the presence of metal salts, such as those disclosed in U.S. Pat. Nos. 4,720,592 and 4,238,415. However, the yield in the production of the cyclohexanol/cyclohexanone mixture is not very high and numerous byproducts are also formed.

U.S. Pat. No. 3,925,316 discloses a process for the decomposition of cyclohexyl hydroperoxide in the presence of homogeneous catalysts composed of soluble vanadium, ruthenium or molybdenum compounds. Other catalytic systems based on pairs of different metals present in the form of soluble compounds are disclosed, for example in U.S. Pat. Nos. 3,401,193, 3,987,100 and 4,551,553.

The decomposition of hydroperoxides in the presence of a homogeneous catalyst has a number of disadvantages. Thus, large amounts of catalyst are entrained and are finally re-encountered either in the product prepared or in the effluents. It is not easy to recover this catalyst and it is therefore necessary to again add fresh catalyst. In addition, the presence of metals, essentially heavy metals, in the effluents is not very favourable to the environment and it is essential to avoid it as far as possible.

A proposal has been made, in attempting to overcome these disadvantages, to carry out this decomposition by heterogeneous catalysis, that is to say in the presence of a catalyst which is not dissolved in the reaction medium.

Thus, U.S. Pat. No. 4,173,587 discloses the use of an insoluble rhenium compound in the decomposition of cumene hydroperoxide.

Patent EP-A-0 492 807 also discloses the preparation of phenol and of acetone from cumyl hydroperoxide in the presence of a zeolite catalyst of mordenite or faujasite type chosen from zeolites Y, thermally stabilized dealuminated zeolites Y, zeolites Y exchanged with rare earth metals, in particular with lanthanum salts, or with transition metals, in particular with cobalt or nickel salts, and zeolites Y treated with fluorides.

In these cases, the metals are again not sufficiently attached to the support and partial dissolution in the reaction medium takes place during the use of the catalysts.

U.S. Pat. No. 4,543,427 discloses the preparation of a cyclohexanol/cyclohexanone mixture which consists in treating a cyclohexyl hydroperoxide with a supported catalyst comprising from 2 to 30% by weight, expressed as cobalt element, of a cobalt oxide deposited or absorbed on a zeolite support. This catalyst is not stable and a significant amount of the metal compound dissolves in the reaction medium. The problems mentioned above for the homogeneous catalyst are then encountered.

Before this, U.S. Pat. No. 2,851,496 disclosed the use of metals from Group VIII, such as cobalt deposited on an alumina, a silica, carbon or kieselguhr, as catalysts for the decomposition of cyclohexyl hydroperoxide. However, this catalyst has a reduced lifetime.

Patent EP 659 726 discloses a process for the preparation of an alcohol/ketone mixture by decomposition of an alkyl hydroperoxide in the presence of a metal immobilized on a support in the presence of an aqueous phase and of a basic compound. The support is a metal oxide, such as $TiO_2$ or $ZrO_2$, on which is deposited a manganese, iron, cobalt and nickel or copper compound.

U.S. Pat. No. 5,298,665 also discloses the use of a catalyst composed of a metal compound deposited on or attached to a support. The compounds of the following metals: cobalt, chromium, vanadium, molybdenum, ruthenium, titanium, manganese and iron, are mentioned as metal compound. The support is a metal oxide chosen from silica, alumina or titanium oxide. This support comprises, at its surface, aromatic or aliphatic amino groups. This catalyst is used to convert an alkyl hydroperoxide to a mixture of alcohol and of ketone.

The catalysts described above have a limited lifetime because, in the majority of cases, the metal element is partially dissolved in the medium, the catalysis mainly being carried out by the dissolved fraction. The supported catalyst becomes exhausted in catalytically active metal and the mixture of ketones/alcohols produced comprises the dissolved metal fraction as harmful impurity.

Patent Application WO-A-94/08932 provides, in order to overcome the disadvantages of the heterogeneous catalysts mentioned above, for the decomposition of organic hydroperoxides to be carried out in the presence of a molecular sieve comprising aluminium and/or silicon and/or phosphorus oxides and a catalysing metal incorporated in the crystal matrix of the said molecular sieve. It seems that the active metal of these heterogeneous catalysts experiences virtually no elution. However, while the problem of elution of the catalyst into the reaction medium thus appears to be solved, it emerges from the patent application itself that the catalyst is rapidly deactivated, which results in the need for reactivation by separation of the catalyst and calcination. In the context of an industrial operation of such a process, it is clear that it is prohibitive to have to frequently separate the catalyst from the reaction medium in order to reactivate it.

One of the aims of the present invention is to overcome these disadvantages by providing a process for the manufacture of a mixture of alcohols and of ketones from an alkyl hydroperoxide comprising a heterogenous catalyst in which the cycle time and lifetime of the catalyst are high and with the reduction of an alcohol/ketone mixture not comprising or comprising a very small amount of metal element used as catalyst.

To this end, the invention provides a process for the manufacture of a mixture of alcohols and/or of ketones by decomposition of an alkyl hydroperoxide in the presence of a catalyst comprising a catalytically active metal element immobilized on a solid support, the said metal element being chosen from the group consisting of the elements belonging to Groups IB to VIIB or VIII of the Periodic Classification (CAS version), including the family of the lanthanides, characterized in that the said metal element is present at the surface of the said solid support in the form of an organometallic part of formula (I) or (II):

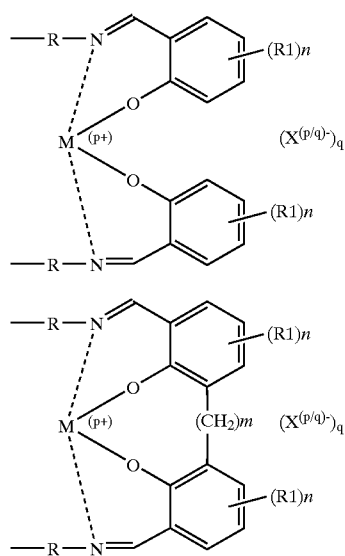

in which:
M is a metal ion or a combination of metal ions corresponding to the elements belonging to Groups IB to VIIB or VIII of the Periodic Classification (CAS version), including the lanthanides, R is a linear or branched hydrocarbonaceous radical comprising from 1 to 12 carbon atoms, $R_1$ is a halogen atom, a hydroxyl radical, an alkoxy radical, a carboxyl radical, an amine radical or an aliphatic, arylaliphatic, aromatic or alkylaliphatic hydrocarbonaceous radical which can comprise heteroatoms, X is an anion, n is an integer between 0 and 4, m is an integer between 1 and 6, p and q are integers between 0 and 4.

In a preferred embodiment of the invention, the metal ion M corresponds to the elements chosen from the following preferred group: chromium, cobalt, copper, iron, manganese, titanium, vanadium, molybdenum, ruthenium, gold and osmium. The preferred elements of the invention are chromium and copper.

The anions which are suitable for the invention are generally anions which form a soluble salt with the metal M in the medium for the preparation of the complex. Mention may be made, by way of examples, of carboxylic anions, such as oxalates or acetates, halides, sulphonates or their mixtures.

Likewise, the support is preferably an inorganic compound, such as inorganic oxides, for example alumina, silica, titanium oxide, zirconium oxide or oxides of rare earth metals, such as cerium oxide or lanthanum oxide, or inorganic compounds, such as lanthanum phosphate. The support can also be chosen from zeolites, molecular sieves of MCM or HMS types, for example, or supports synthesized from functionalized polymers, such a polystyrenes or polyacrylonitriles, for example. More generally, any solid porous structure may be suitable for the present invention.

Mention may in particular be made, as catalysts in accordance with the invention, of those described in the article by J. H. Clark et al. "Catalytic oxidation of alkyl aromatic using a novel silica supported Schiff base complex" published in the review J. Chem. Commun., 1998, pages 1941–1950.

These catalysts are preferably obtained by a solution process in which the metal complex, preformed beforehand, is attached to the surface of the support and more particularly of silica in the final stage of synthesis. This synthetic process has in particular the advantage of forming a metal complex in a simple way by using a suitable solvent.

The support is subsequently added to the medium in which the complex has been formed, in order to allow the latter to become attached to the said support.

Mention may be made, as examples of metal complex, of those corresponding to the general formulae (III) and (III)$_a$ below:

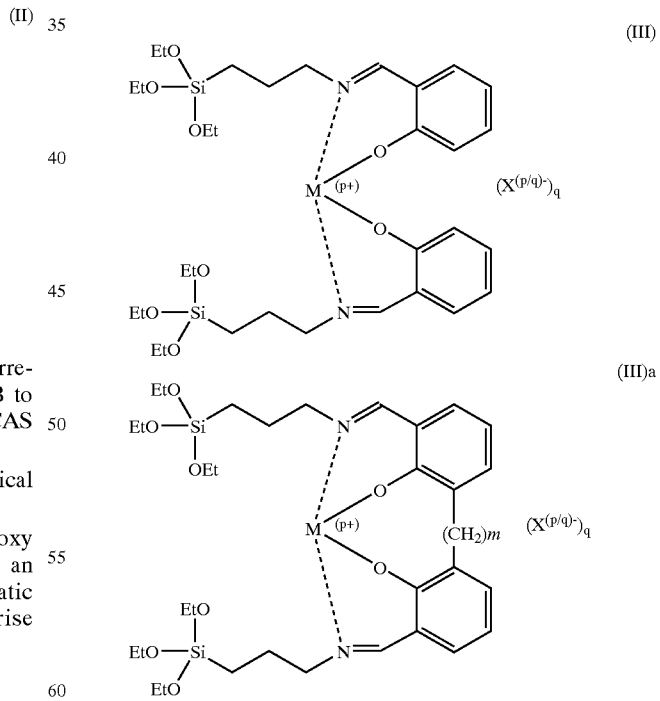

In these formulae, m, p and q have the meanings indicated above.

The catalyst prepared according to this process exhibits a better catalytic activity than those formed by attachment of the ligand to the support and then, in a final stage, addition of the metal ions in order to form the complex.

Another embodiment of a catalyst in accordance with the invention consists in adding, to a liquid medium, a precursor of a gel of the solid support and the compounds needed for the formation of the metal complex described above. The medium is subsequently modified in order to bring about the formation of the gel, for example by modifying the pH or addition of a cosolvent. This modifying of the medium can be obtained during the addition of one of the compounds needed for the formation of the complex.

These synthetic processes are described in the article indicated above and are only given by way of example and of illustration.

Mention may be made, as example of a catalyst thus synthesized, of the catalyst in which the organometallic part has the following formula (IV):

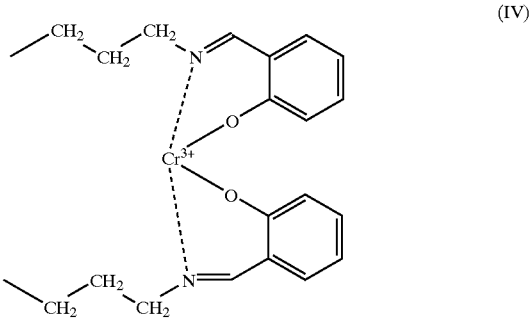

(IV)

These catalysts, used in the process for the decomposition of alkyl hydroperoxides, exhibit a very good activity and a very good selectivity for alcohols and ketones. This activity and this selectivity are greater than those observed with a homogeneous chromium catalyst.

In addition, the lifetime of the catalyst is long as a deactivation phenomenon has not been demonstrated.

Finally, the amount of metal eluted during the decomposition reaction is very low, which makes it possible, on the one hand, to reduce the amount of metal to be involved and, on the other hand, to limit the presence of metal contaminant in the ketone/alcohol mixture produced or in the discharges from the process.

The invention applies in particular to the decomposition of the alkyl hydroperoxides produced by air oxidation of an alkane comprising from 3 to 30 carbon atoms.

This reaction is generally carried out in a solvent medium.

The oxidation of the alkanes is carried out under conventional conditions widely described in the literature. By way of illustration, this oxidation can be carried out in the liquid phase in the presence of pure oxygen, of air or of a mixture enriched in oxygen at a temperature of between 80° C. and 250° C.

Generally, in processes for the oxidation of alkanes, the degree of conversion of the latter is between 1 and 50% by weight approximately.

This oxidation can be carried out in the absence of catalyst or with an oxidation catalyst chosen from transition metals, such as cobalt, chromium, manganese, iron, nickel, copper or a mixture of these.

The alkyl hydroperoxide formed is generally soluble in the corresponding alkane which is used as solvent. However, it is possible to use other solvents, such as alcohols or ketones and in particular the alcohols and ketones produced by the reaction for the decomposition of the hydroperoxide.

The reaction for the decomposition of the alkyl hydroperoxide is subsequently carried out in the presence of the supported catalyst described above. This catalyst is employed in the form of a stationary or fluidized bed or in suspension in the medium. This decomposition can be carried out directly in the medium resulting from the oxidation, after washing the said reaction medium with water, or after extracting the hydroperoxide.

The temperature of the decomposition reaction is maintained between 25 and 200° C., preferably between 70 and 150° C. approximately, for example at the temperature of evaporation of the alkane or of the solvent, with reflux of the latter.

The amount of catalyst involved depends on the embodiment. Thus, as a stationary bed, the amount of catalyst is higher than that used in the use of a suspended catalyst.

Likewise, the concentration of hydroperoxide can vary within wide limits.

The products obtained are mainly alcohols and ketones, which can be separated and extracted from the reaction medium by distillation, if necessary.

It is also possible to subject the reaction medium to a fresh oxidation, for example with nitric acid, in order to manufacture adipic acid.

This reaction medium can also be employed as starting material for the synthesis of caprolactam.

The alkanes which can be oxidized are in particular cycloalkanes or linear or branched alkanes comprising from 3 to 30 carbon atoms.

Mention may be made, by way of examples, of propane, cyclohexane, cycloheptane, methylbenzene, ethylbenzene, phenylcyclohexane, diphenylmethane, phenylcyclododecane, cyclododecane, 1,2-dicyclohexylmethane, cumene, isobutane, 2-methylpropane, 2-propylbenzene, cyclohexene, 4-tert-butyl-1-cycloheptylbenzene, 2-isopropylnaphthalene, fluorene or 1,8-dimethylfluorene.

The process applies more particularly to the oxidation of cyclohexane and the decomposition of cyclohexyl hydroperoxide to cyclohexanone/cyclohexanol.

It also applies to the decomposition of an alkyl hydroperoxide obtained by processes other than that of the oxidation of an alkane.

The invention will be more fully illustrated in the light of the examples, given below, purely by way of indication.

Three catalysts A, B and C are manufactured according to the processes described in Examples 1 to 3.

These catalysts comprise a chromium complex forming an organometallic part attached to a silica support.

EXAMPLE 1

Preparation of Catalyst A

Salicylaldehyde is added to ethanol with 3-aminopropyl (trimethoxy)silane. The solution instantaneously becomes yellow. Chromium acetate is added to the solution and the mixture is stirred for 30 minutes in order to allow the formation of the complex with the following formula:

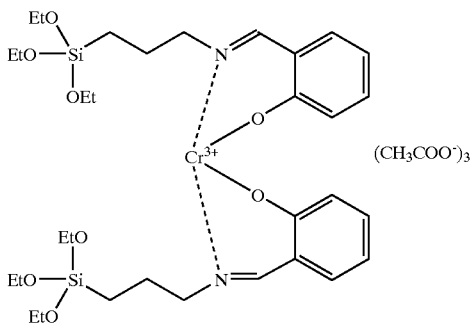

Silica sold under the name Kieselgel 100 is added to the medium, which is kept stirred overnight.

The final product is extracted by filtration and is washed with water and alcohol.

The product is dried at 70° C. for two hours.

The catalyst obtained exhibits a mean pore diameter of 100□ and particles with a size between 30 and 140 μm.

The molar concentration of chromium is 0.106 mmol per gram of catalyst (0.57% by weight).

EXAMPLE 2

Preparation of Catalyst B

Example 1 is repeated but using an HMS mesoporous silica as support instead of the Kieselgel silica.

The HMS mesoporous silica is obtained according to the following process:

0.054 mol of dodecylamine are added to a water/ethanol mixture (11.8 mol of water and 3.6 mol of ethanol). The solution is stirred for 20 minutes with addition of 0.4 mol of tetraethoxysilane. The white precipitate obtained after maturing for 18 hours is filtered off, dried and calcined at a temperature of 600° C. for 4 hours in order to remove the organic compounds. Other amines can be used, such as decylamine.

The catalyst obtained comprises 0.36 mmol of chromium per gram of catalyst (1.80% by weight).

EXAMPLE 3

Preparation of Catalyst C by a Sol-gel Method 0.02 mol of salicylaldehyde and 0.02 mol of aminopropyl (trimethoxy)silane are added to pure ethanol. 10 mmol of chromium acetate are added to the solution, which is kept stirred for 30 minutes. Another solution is prepared by addition of 0.049 mol of dodecylamine to 100 ml of water. Pure ethanol is gradually added to the latter solution until the dodecylamine has completely dissolved.

The two solutions thus prepared are mixed with immediate addition of tetraethoxysilane (0.255 mol). The mixture obtained is kept stirred overnight.

The green solid formed is filtered off and washed with water and ethanol. The solid thus obtained is treated with ethanol and then dried at 70° C. in order to remove the solvent.

The catalyst obtained comprises 0.073 mmol of Cr per gram of catalyst (0.52% by weight).

EXAMPLE 4

Decomposition of Cyclohexyl Hydroperoxide (CHHPO)

The solution to be treated results from the oxidation by air of cyclohexane at 180° C. It comprises 6.09% of cyclohexyl hydroperoxide, 1.36% by weight of cyclohexanone and 1.37% by weight of cyclohexanol.

40 g of this solution are heated at 80° C. with azeotropic distillation of the water in the presence of 1 g of catalyst.

The nature of the catalyst added and the reaction duration are shown in Table 1 below, along with the yields for conversion and for production of the various chemical compounds.

The various concentrations of cyclohexanone, cycolohexanol and CHHPO are determined by the following methods:

Quantitative determination of the cyclohexyl hydroperoxide:

The principle is the oxidation of potassium iodide by the hydroperoxide and back-titration of the iodine formed with a sodium thiosulphate solution.

Quantitative determination of the concentrations of ketone and alcohol:

The quantitative determination is carried out by a chromatographic method after reduction of the hydroperoxide present to alcohol by reaction with a triphenylphosphine.

The chromatographic analysis gives the total concentration of ketones and the total concentration of alcohols.

The concentration of ketone formed and the concentration of alcohol formed are calculated by taking into account the initial concentrations of ketone and of alcohol and the concentration of the residual hydroperoxide.

In Table I below:

DC means the degree of conversion of the cyclohexyl hydroperoxide in %;

YDone means the selectivity of the reaction for ketone compounds (expressed as amount of ketone, expressed as cyclohexanone, formed by the decomposition of the CHHPO with respect to the theoretical amount of cyclohexanone formed, calculated from the actual amount of CHHPO converted);

YDol means the yield of alcohol compounds (expressed as amount of alcohol, expressed as cyclohexanol, formed by the decomposition of the CHHPO with respect to the theoretical amount of cyclohexanol formed, calculated from the actual amount of CHHPO converted);

One/Ol: molar ratio of ketone/alcohol.

| Test | Catalyst | Duration (min) | DC | YDone | YDol | One/Ol |
| --- | --- | --- | --- | --- | --- | --- |
| 4 | A | 70 | 98.8 | 65/0 | 51.5 | 1.26 |
| 5 | B | 60 | 98.5 | 66.4 | 44.8 | 1.5 |
| 6 | C | 60 | 99.1 | 67.2 | 37.4 | 1.8 |

By way of comparison, a test was carried out with a homogeneous chromium-based catalyst (di-tert-butyl chromate) with a CHHPO/Cr ratio of 6 550. A degree of conversion (DC) of 94% was achieved after 90 minutes with a high selectivity for cyclohexanone (YDone=81.6%; YDol=26.6%; One/Ol ratio=3.1).

Furthermore, analysis of the chromium eluted into the reaction medium shows that the concentrations of Cr are very low (less than 1 ppm) in Examples 4 to 6 (catalysts A, B, C of the invention).

EXAMPLE 7

Catalyst A used in Example 4 was recovered after the 70 minutes of reaction. A further test on the decomposition of cyclohexyl hydroperoxide was carried out according to the conditions of Example 4 but using the recovered catalyst as catalyst. The data on the progress of the reaction are given in Table II below:

| Test | Catalyst | Duration (min) | DC | YDone | YDol |
|---|---|---|---|---|---|
| 7 | Recovered A | 5 | 47.6 | | |
| | | 40 | 97.7 | | |
| | | 60 | 98.5 | 66.4 | 44.8 |
| 4 | A | 5 | 9.4 | | |
| | | 30 | 53.8 | | |
| | | 70 | 98.8 | 65 | 51.5 |

In addition, in Example 4 above, the concentration of chromium eluted is of the order of 0.7 mg/kg of solution, i.e. 0.47% of the chromium involved is eluted. In Example 7, this concentration is less than 0.1 mg/kg of solution, i.e. a percentage of chromium eluted of less than 0.07%.

What is claimed is:

1. A process for the manufacture of a ketone/alcohol mixture by decomposition of an alkyl hydroperoxide in the presence of a catalyst comprising a catalytically active metal element immobilized on a solid support, wherein the catalyst comprises an organometallic part of general formula (I) or (II):

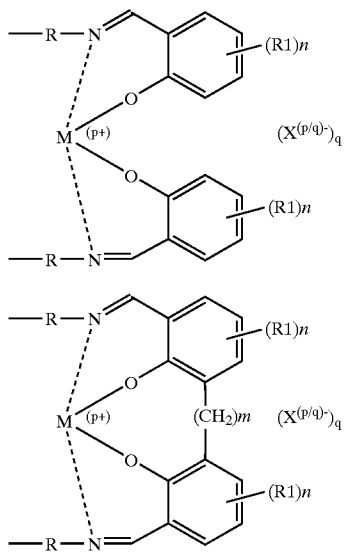

in which:

M is a metal ion or a combination of metal ions corresponding to the elements belonging to Groups IB to VIIB or VIII to of Periodic Classification (CAS version), including the lanthanides, R is a linear or branched hydrocarbonaceous radical comprising from 1 to 12 carbon atoms, $R_1$ is a halogen atom, a hydroxyl radical, an alkoxy radical, a carboxyl radical, an amine radical or aliphatic, arylaliphatic, aromatic or alkylaliphatic hydrocarbonaceous radical which can comprise heteroatoms, X is an anion, n is an integer between 0 and 4, m is an integer between 1 and 6, p and q are integers between 0 and 4.

2. The process according to claim 1, wherein the metal element M is selected from the group consisting of chromium, cobalt, iron, manganese, titanaium, copper, vanadium, molybdenum, ruthenium, gold and osmium.

3. The process according to claim 1, wherein the solid support is an inorganic oxide, selected from the group consisting of alumina, silica, zirconium oxide, oxides of rare earth metals and titanium oxide, or inorganic compounds, zeolites, molecular sieves or supports synthesized from functionalized polymers.

4. The process according to claim 1, wherein the catalyst is obtained by manufacture of a metal complex of general formula (III) or (III)a:

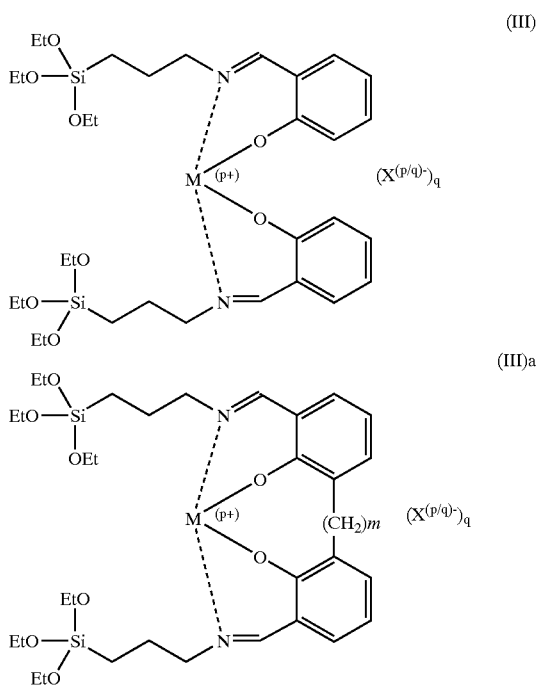

in a solvent and grafting the complex to the support by bringing the complex and the support into contact.

5. The process according to claim 4, wherein the solid support is produced in situ in the solution in the form of a gel.

6. The process according to claim 1, wherein the alkyl hydroperoxide is obtained by oxidation of an alkane by an oxidizing agent.

7. The process according to claim 6, wherein the oxidizing agent is selected from the group consisting of oxygen, air and mixtures enriched in oxygen.

8. The process according to claim 6, wherein the alkane comprises from 3 to 30 carbon atoms and is selected from the group consisting of propane, cyclohexane, cycloheptane, methylbenzene, ethylbenzene, phenylcyclohexane, diphenylmethane, phenylcyclododecane, cyclododecane, 1,2-dicyclohexylmethane, cumene, isobutane, 2-methylpropane, 2-porpylbenzene, cyclohexene, 4-tert-butyl-1-cycloheptylbenzene, 2-isopropylnaphthalene, fluorene and 1,8-dimethylfluorene.

9. The process according to claim 1, which comprises a stage of production of cyclohexyl hydroperoxide by oxidation of cyclohexane and decomposition of the hydroperoxide to cyclohexane and/or cyclohexanol.

* * * * *